(12) United States Patent
Poplett

(10) Patent No.: US 7,532,456 B2
(45) Date of Patent: May 12, 2009

(54) METHOD AND APPARATUS FOR A PARTIALLY ETCHED CAPACITOR LAYER INCLUDING A CONNECTION MEMBER

(75) Inventor: James M. Poplett, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/379,284

(22) Filed: Apr. 19, 2006

(65) Prior Publication Data

US 2006/0179626 A1   Aug. 17, 2006

Related U.S. Application Data

(63) Continuation of application No. 11/065,873, filed on Feb. 25, 2005, now Pat. No. 7,180,727.

(51) Int. Cl.
*H01G 9/04* (2006.01)
(52) U.S. Cl. .................. 361/508; 361/303; 361/528; 361/532
(58) Field of Classification Search ............ 361/503, 361/508, 510, 517, 520, 522, 528, 529, 538
See application file for complete search history.

(56) References Cited

U.S. PATENT DOCUMENTS

| | | | |
|---|---|---|---|
| 4,171,477 A | 10/1979 | Funari | |
| 4,676,879 A | 6/1987 | Salvadori | |
| 5,195,019 A | 3/1993 | Hertz | |
| 5,384,685 A | 1/1995 | Tong et al. | |
| 5,660,737 A | 8/1997 | Elias et al. | |
| 5,748,438 A | 5/1998 | Davis et al. | |
| 5,801,917 A | 9/1998 | Elias | |
| 5,808,857 A | 9/1998 | Stevens | |
| 5,814,082 A | 9/1998 | Fayram et al. | |
| 5,821,033 A | 10/1998 | Cromack et al. | |
| 5,908,151 A | 6/1999 | Elias | |
| 5,922,215 A | 7/1999 | Pless et al. | |
| 5,930,109 A | 7/1999 | Fishler | |
| 5,963,418 A | 10/1999 | Greenwood, Jr. et al. | |
| 5,968,210 A | 10/1999 | Strange et al. | |

(Continued)

FOREIGN PATENT DOCUMENTS

GB        825900        12/1959

(Continued)

OTHER PUBLICATIONS

"U.S. Appl. No. 10/996,903, Non-Final Office Action mailed Jul. 5, 2007", 9 Pages.

(Continued)

*Primary Examiner*—Eric Thomas
(74) *Attorney, Agent, or Firm*—Schwegman, Lundberg & Woessner, P.A.

(57) ABSTRACT

An apparatus which includes a capacitor stack including a plurality of substantially planar electrodes, a first partially etched anode layer of the capacitor stack including a first substantially unetched portion, a second anode layer of the capacitor stack, a first connection member connected to the first substantially unetched portion and a second connection member connected to the second anode layer and the first connection member.

21 Claims, 6 Drawing Sheets

U.S. PATENT DOCUMENTS

| | | | |
|---|---|---|---|
| 5,980,977 A | 11/1999 | Deng et al. | |
| 5,983,472 A | 11/1999 | Fayram et al. | |
| 6,004,692 A | 12/1999 | Muffoletto et al. | |
| 6,009,348 A * | 12/1999 | Rorvick et al. | 607/5 |
| 6,032,075 A | 2/2000 | Pignato et al. | |
| 6,040,082 A | 3/2000 | Haas et al. | |
| 6,094,788 A | 8/2000 | Farahmandi et al. | |
| 6,099,600 A | 8/2000 | Yan et al. | |
| 6,110,233 A | 8/2000 | O'Phelan et al. | |
| 6,110,321 A | 8/2000 | Day et al. | |
| 6,118,652 A | 9/2000 | Casby et al. | |
| 6,139,986 A | 10/2000 | Kurokawa et al. | |
| 6,141,205 A | 10/2000 | Nutzman et al. | |
| 6,157,531 A | 12/2000 | Breyen et al. | |
| 6,191,931 B1 | 2/2001 | Paspa et al. | |
| 6,212,063 B1 | 4/2001 | Johnson et al. | |
| 6,225,778 B1 | 5/2001 | Hayama et al. | |
| 6,275,729 B1 | 8/2001 | O'Phelan et al. | |
| 6,299,752 B1 | 10/2001 | Strange et al. | |
| 6,321,114 B1 | 11/2001 | Nutzman et al. | |
| 6,402,793 B1 | 6/2002 | Miltich et al. | |
| 6,409,776 B1 | 6/2002 | Yan et al. | |
| 6,421,226 B1 | 7/2002 | O'Phelan et al. | |
| 6,426,864 B1 | 7/2002 | O'Phelan et al. | |
| 6,445,948 B1 | 9/2002 | Somdahl et al. | |
| 6,451,073 B1 | 9/2002 | Farahmandi et al. | |
| 6,493,212 B1 | 12/2002 | Clarke et al. | |
| 6,509,588 B1 | 1/2003 | O'Phelan et al. | |
| 6,522,525 B1 | 2/2003 | O'Phelan et al. | |
| 6,556,863 B1 | 4/2003 | O'Phelan et al. | |
| 6,571,126 B1 | 5/2003 | O'Phelan et al. | |
| 6,585,152 B2 | 7/2003 | Farahmandi et al. | |
| 6,674,634 B2 | 1/2004 | O'Phelan et al. | |
| 6,684,102 B1 | 1/2004 | O'Phelan et al. | |
| 6,687,118 B1 | 2/2004 | O'Phelan et al. | |
| 6,699,265 B1 | 3/2004 | O'Phelan et al. | |
| 6,709,946 B2 | 3/2004 | O'Phelan et al. | |
| 6,736,956 B1 | 5/2004 | Hemphill et al. | |
| 6,833,987 B1 | 12/2004 | O'Phelan | |
| 7,072,713 B2 | 7/2006 | O'Phelan et al. | |
| 7,180,727 B2 | 2/2007 | Poplett | |
| 7,419,873 B2 | 9/2008 | Doffing et al. | |
| 2003/0072124 A1 | 4/2003 | O'Phelan et al. | |
| 2003/0077509 A1 | 4/2003 | Probst et al. | |
| 2003/0195568 A1 | 10/2003 | O'Phelan et al. | |
| 2004/0019268 A1 | 1/2004 | Schmidt et al. | |
| 2004/0039421 A1 | 2/2004 | O'Phelan et al. | |
| 2004/0114311 A1 | 6/2004 | O'Phelan et al. | |
| 2004/0127952 A1 | 7/2004 | O'Phelan et al. | |
| 2004/0147960 A1 | 7/2004 | O'Phelan et al. | |
| 2004/0147961 A1 | 7/2004 | O'Phelan et al. | |
| 2004/0173835 A1 | 9/2004 | Schmidt et al. | |
| 2004/0174658 A1 | 9/2004 | O'Phelan et al. | |
| 2004/0215281 A1 | 10/2004 | O'Phelan et al. | |
| 2004/0220627 A1 | 11/2004 | Crespi et al. | |
| 2005/0010253 A1 | 1/2005 | O'Phelan et al. | |
| 2005/0017888 A1 | 1/2005 | Sherwood et al. | |
| 2005/0052825 A1 | 3/2005 | O'Phelan | |
| 2006/0012942 A1 | 1/2006 | Poplett | |
| 2006/0107506 A1 | 5/2006 | Doffing et al. | |
| 2006/0174463 A1 | 8/2006 | O'Phelan et al. | |

FOREIGN PATENT DOCUMENTS

| | | | |
|---|---|---|---|
| JP | 52-004051 | | 1/1977 |
| JP | 59-083772 | | 5/1984 |
| JP | 2002231582 A | * | 8/2002 |
| WO | WO-99/66985 | | 12/1999 |
| WO | WO-00/19470 | | 4/2000 |

OTHER PUBLICATIONS

Porter, Mark C., "Handbook of Industrial Membrane Technology", *Handbook of Industrial Membrane Technology, Noyes Publications*, (1990), 623 Pages.

Doffing, B., et al., "Method and Apparatus for Providing Flexible Partially Etched Capacitor Electrode Interconnect", U.S. Appl. 10/996,903, filed Nov. 24, 2004, 239 Pgs.

Morley, A. R., et al., "Electrolytic capacitors: their fabrication and the interpretation of their operations behaviour", *The Radio and Electronic Engineer*, vol. 43, No. 7,(Jul. 1973),421-429.

Schmidt, Brian L., et al., "Configurations and Methods for Making Capacitor Connections", U.S. Appl. No. 09/706,576, filed Nov. 3, 2000, 26 pgs.

Schmidt, Brian, et al., "Method for Interconnecting Anodes and Cathodes in a Flat Capacitor", U.S. Appl. No. 11/325,931, filed Jan. 5, 2006, 28 Pages.

"U.S. Appl. No. 10/996,903, Response filed Jan. 30, 2008 to Non-Final Office Action mailed Nov. 2, 2007", 9 pgs.

"U.S. Appl. No. 10/996,903, Response filed Oct. 5, 2007 to Office Action mailed Jul. 5, 2007", 8 pgs.

"Non-Final Office Action mailed Nov. 2, 2007 in U.S. Appl. No. 10/996,903", 7 pgs.

"U.S. Appl. No. 10/996,903 Notice of Allowance mailed Apr. 30, 2008", 8 pgs.

* cited by examiner

METHOD AND APPARATUS FOR A PARTIALLY ETCHED CAPACITOR LAYER INCLUDING A CONNECTION MEMBER

CROSS REFERENCE TO RELATED APPLICATIONS

The present application is a continuation U.S. patent application Ser. No. 11/065,873, filed on Feb. 25, 2005, now issued as U.S. Pat. No. 7,180,727, the specification of which is incorporated herein by reference.

The present application is related to the following commonly assigned U.S. Patents which are incorporated by reference in their entirety: "High-Energy Capacitors for Implantable Defibrillators," U.S. Pat. No. 6,556,863, filed Oct. 2, 1998, issued Apr. 29, 2003; "Flat Capacitor for an Implantable Medical Device," U.S. Pat. No. 6,699,265, filed Nov. 3, 2000, issued Mar. 2, 2004. Additionally, the present application is related to the following Provisional U.S. Patent Application which is assigned to the same assignee and is incorporated by reference in its entirety: "Method and Apparatus for High Voltage Aluminum Capacitor Design," Ser. No. 60/588,905, filed on Jul. 16, 2004.

TECHNICAL FIELD

This disclosure relates generally to capacitors, and more particularly, to a method and apparatus for a partially etched capacitor layer including a connection member.

BACKGROUND

There is an ever-increasing interest in making electronic devices physically smaller. Consequently, electrical components become more compact as technologies are improved. However, such advances in technology also bring about additional problems. One such problem involves interconnects between various components and interconnects within components.

Interconnects are especially problematic with devices incorporating multiple layers. One such component is the capacitor. Capacitors provide improved charge storage and energy density using multiple conductive layers and advanced dielectrics. As the layers become more complex and smaller in dimensions, problems arise with interconnections.

Thus, there is a need in the art for improved technologies for interconnects between layered devices. The systems used to interconnect the multiple layers should be readily adapted for manufacturing. The interconnects should form robust connections without damaging the multiple layers and without sacrificing substantial performance of the component.

SUMMARY

The above-mentioned problems and others not expressly discussed herein are addressed by the present subject matter and will be understood by reading and studying this specification.

One embodiment of the present subject matter includes an apparatus which includes a capacitor stack including a plurality of substantially planar electrodes, a first partially etched anode of the capacitor stack including a first substantially unetched portion, a second anode of the capacitor stack, a first connection member joined to the first substantially unetched portion and a second connection member joined to the second anode and the first connection member.

One embodiment of the present subject matter includes an apparatus which includes a first substantially planar capacitor electrode, a second substantially planar capacitor electrode in stacked alignment with the first substantially planar capacitor electrode, and joining means for joining the first substantially planar capacitor electrode to the second substantially planar capacitor electrode, wherein the first substantially planar capacitor electrode includes surface means for joining the first substantially planar capacitor electrode to the joining means.

One embodiment of the present subject matter includes a capacitor stack including a first substantially planar anode which includes a first substantially unetched portion, with a first connection member joined to the first substantially unetched portion, a second substantially planar anode connected to a second connection member, with the first connection member and the second connection member joined, the first substantially unetched portion produced by a process including depositing a curable resin mask onto an electrode, curing the curable resin mask to the electrode, etching the electrode, the cured mask restricting the etch, removing the cured mask from the electrode and anodizing the electrode.

One embodiment of the present subject matter includes a method, including attaching a first connection member to an unetched connection area, the unetched connection area located on a single major surface of a first planar anode, forming a capacitor stack by aligning the first planar anode with at least a second planar anode, the second planar anode including at least a second connection member, the first connection member and the second connection member for electrical connection of the first planar anode to the second planar anode, aligning the first connection member and the second connection member to define an anode connection surface and joining the first planar anode and the second planar anode.

Various optional configurations are possible within the present scope. Some optional embodiments within the present scope include welds formed by stake welding and welds formed by laser welding. An interconnection member can be welded to planar electrodes in some optional embodiments. Some optional embodiments organize planar electrodes into elements. Some optional embodiments align multiple planar electrodes before welding. Some optional embodiments include a capacitor adapted to provide from about 5.3 joules per cubic centimeter of capacitor stack volume to about 6.3 joules per cubic centimeter of capacitor stack volume. Some optional embodiments include a capacitor adapted to provide approximately 5.8 joules per cubic centimeter of capacitor stack volume. Other options are possible without departing from the scope of the present subject matter.

This Summary is an overview of some of the teachings of the present application and is not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references may contemplate more than one embodiment. The following detailed description is, therefore, not to be taken in a limiting sense, and the scope is defined only by the appended claims, along with the full scope of legal equivalents to which such claims are entitled.

Figure 1:
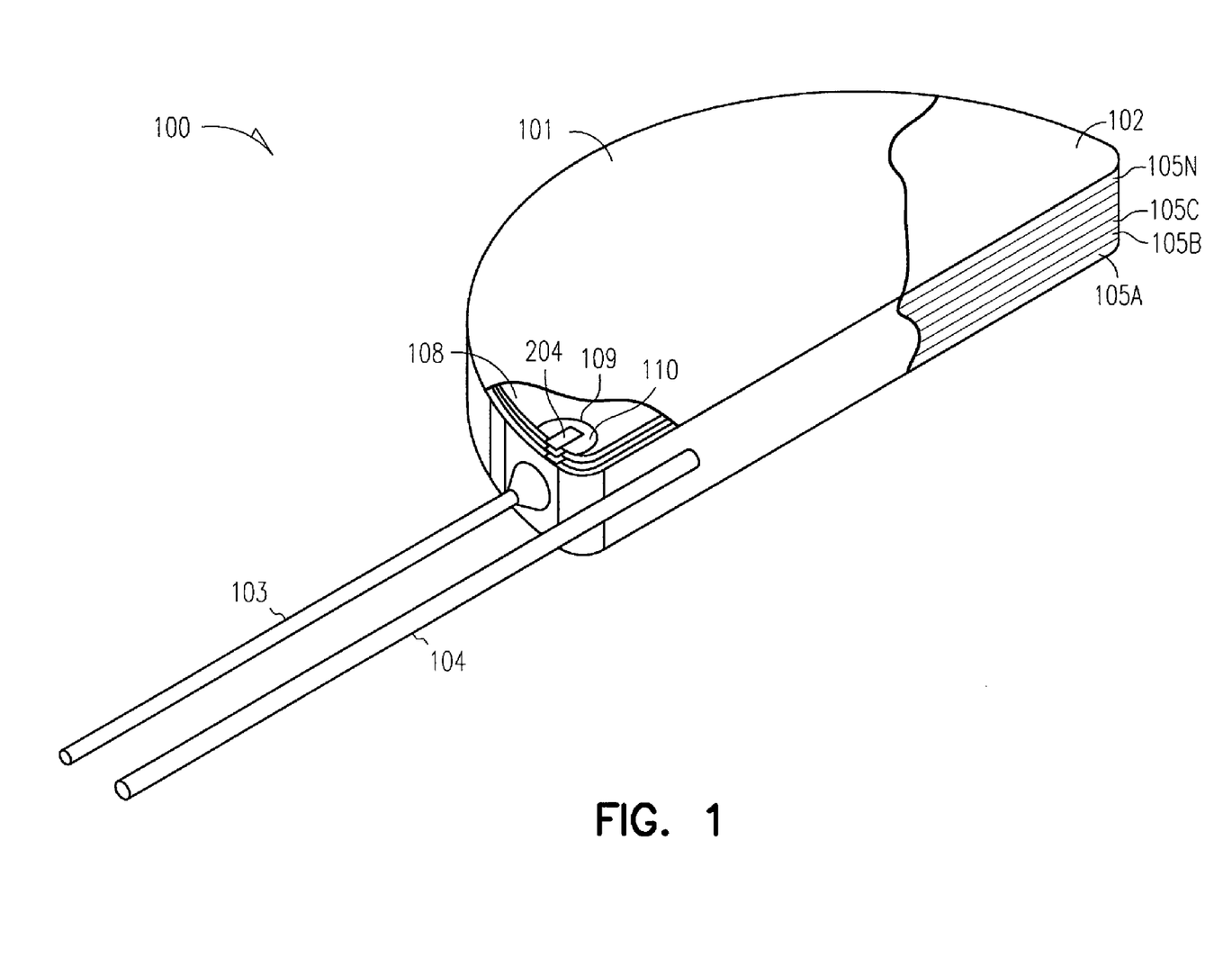
FIG. 1 is a perspective view of a capacitor according to one embodiment of the present subject matter.

FIG. 1 shows a flat capacitor 100 constructed according to one embodiment of the present subject matter. Although capacitor 100 is a D-shaped capacitor, in various embodiments, the capacitor is another desirable shape, including, but not limited to rectangular, circular, oval or other symmetrical or asymmetrical shape. Capacitor 100 includes a case 101 which contains a capacitor stack 102. In one embodiment, case 101 is manufactured from a conductive material, such as aluminum. In additional embodiments, the case is manufactured using a nonconductive material, such as a ceramic or a plastic.

In various embodiments, capacitor 100 includes a first terminal 103 and a second terminal 104 for connecting capacitor stack 102 to an outside electrical component, such as heart monitor circuitry, including defibrillator, cardioverter, and pacemaker circuitry. In one embodiment, terminal 103 is a feedthrough terminal insulated from case 101, while terminal 104 is directly connected to case 101. In various embodiments, the capacitor incorporates additional connection structures and methods. Additional connection structures and methods, such as embodiments including two or more feedthrough terminals as described on or around pages 12-13, 59-60, 63-82 of Provisional U.S. Patent Application, "Method and Apparatus for High Voltage Aluminum Capacitor Design," Ser. No. 60/588,905, filed on Jul. 16, 2004, are incorporated herein by reference, but not by way of limitation.

Capacitor stack 102 includes, in various embodiments, capacitor elements 105A, 105B, 105C, . . . , 105N, with each capacitor element 105A-105N including one or more cathodes, anodes, and separators. In various embodiments, each cathode is a foil structure and/or case include aluminum, tantalum, hafnium, niobium, titanium, zirconium, and combinations of these metals. In some embodiments, each cathode of capacitor stack 102 is connected to the other cathodes by welding or other connection methods. Additionally, in some embodiments, the cathodes are coupled to conductive case 101, and terminal 104 is attached to case 101 to provide a cathode connection to outside circuitry. In one embodiment, the cathode is coupled to a feedthrough conductor extending through a feedthrough hole.

Pictured in the example is an anode with an etched section 108, the anode having an unetched portion 110. Etching is discussed in various degrees throughout this application. Generally, etching as used herein relates to using chemicals to remove material. One specific form of etching which applies in various embodiments of the present subject matter involves roughening the surface of an electrode before growing a dielectric on the electrode. Following, in some embodiments, a dielectric coating is substantially absent from the unetched portion 110, and in additional embodiments a dielectric coating is present at unetched portion 110.

In various embodiments, the etch gradient is structured to reduce bending stress at the etch gradient 109. Etch gradient structure are described on or around pages 32-34, 115-119 of Provisional U.S. Patent Application Ser. No. 60/588,905. The teachings of those pages are incorporated herein by reference, but not by way of limitation.

A separator is located between each anode and cathode, in various embodiments. In one embodiment, the separator includes one or more sheets of kraft paper impregnated with an electrolyte. In one embodiment, the separator includes two sheets of paper. The electrolyte can be any suitable electrolyte for an electrolytic capacitor, such as an ethylene-glycol base combined with polyphosphates, ammonium pentaborate, and/or an adipic acid solute.

In one embodiment, one or more of the anodes of capacitor stack 102 are configured into an element which includes three foil layers. In various embodiments, an element include one, two, three or more anode foils having a variety of anode shapes. In various embodiments, anodes are generally foil structures and can include aluminum, tantalum, hafnium, niobium, titanium, zirconium, and combinations of these metals. In one embodiment, at least portions of a major surface of each anode foil is roughened and/or etched to increase its effective surface area. An etch may be measured using a surface roughness measurement, for example. Roughness imparted on the surface increases the capacitive effect of the foil with no relative increase in volume. Various embodiments incorporate other foil compositions and/or classes of foil compositions.

In various embodiments, the present subject matter includes anodes which have unetched portions on a single side of an anode layer. In some embodiments, these single-sided portions are substantially constrained to a single approximately planar face of an anode. Additionally, single sided portions in some embodiments are primarily constrained to a first approximately planar face of an anode, with sections of the unetched portion extending to second approximately planar face of the anode. In one embodiment, each anode is connected to the other anodes of the capacitor and is coupled to feedthrough assembly 103 for electrically connecting the anode to circuitry outside the case. In some embodiments, the anodes are connected to the case and the cathodes are coupled to a feedthrough assembly. In various embodiments, both the anode and the cathode are connected to components through feedthroughs.

Various embodiments include a capacitor stack adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

In various embodiments, the stack is disposed in a case, and linked with other components, a state which affects some of these values. For example, in one packaged embodiment, including a case and terminals, the energy density available ranges from about 5.3 joules per cubic centimeter of capacitor stack volume to about 6.3 joules per cubic centimeter of capacitor stack volume. Some embodiments are adapted to deliver about 5.8 joules. In various embodiments, these ranges are available at a voltage of between about 410 volts to about 610 volts.

Attached to anode stack 102 is a connection structure such as a tab or connection member 204. In various embodiments, the connection member 204 is made from aluminum, which electrically connects each anode foil to the other anodes of the capacitor. In various embodiments, multiple anodes include multiple connected connection members. For instance, in the present embodiment, each connection member 204 of each capacitor element 105A, . . . , 105N is connected to each another connection member 204 and coupled to terminal 103 for electrically coupling the anode to a component or electronic assembly outside the case 101.

Figure 2:
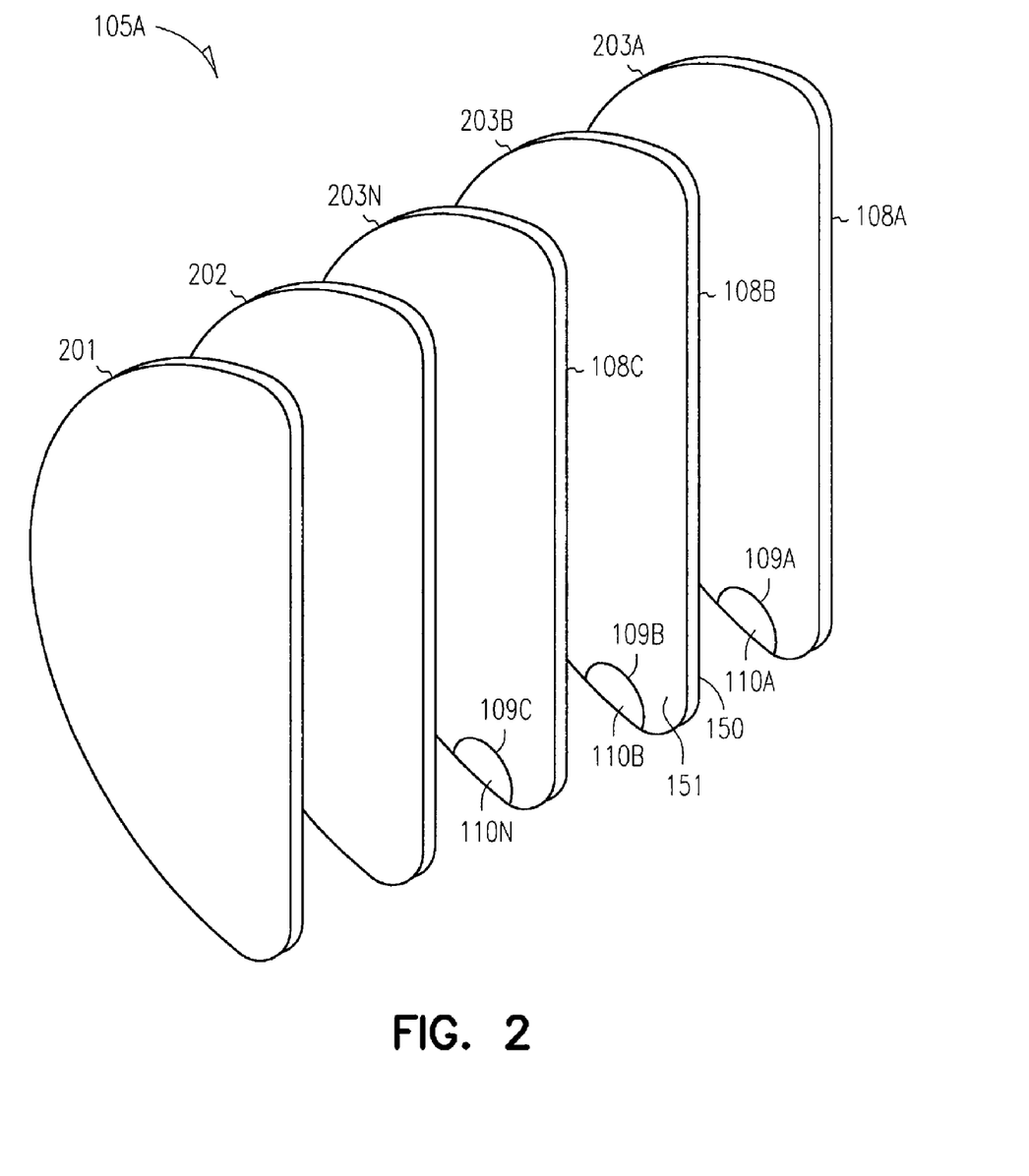
FIG. 2 is an exploded perspective view of a capacitor element, according to one embodiment of the present subject matter.

FIG. 2 shows details of one example of capacitor element 105a, which is representative of capacitor elements 105B-105N illustrated in the example FIG. 1. Element 105A includes a cathode 201, a separator 202, and an anode stack including anode layers 203A, 203B, . . . , 203N. In various embodiments, other numbers and arrangements of anodes, cathodes, and separators are utilized. Related Provisional U.S. Patent Application "Method and Apparatus for High Voltage Aluminum Capacitor Design," Ser. No. 60/588,905, filed on Jul. 16, 2004 discusses additional methods on or around pages 13-29 which are incorporated here by reference, but not by way of limitation.

For explanation, number flags of the present illustration match the example illustrated in FIG. 1, but this relationship should not be interpreted as limiting. Cathode 201 is a foil attached to other cathodes of capacitor stack 102 and to terminal 104 of the example FIG. 1. In some embodiments, cathode 201 can include aluminum, tantalum, hafnium, niobium, titanium, zirconium, and combinations of these metals. In one embodiment, cathode 201 is constructed by taking an aluminum (98% purity or higher) base metal and coating it with titanium oxide, titanium nitride, or titanium pentoxide using sputtering, plating, vacuum deposition, or other coating techniques. In some embodiments, titanium itself is used with a subsequent processing step used to oxidize the titanium resulting in $TiO$, $TiO_2$, $TiN$, $Ti_2O_5$, or other high dielectric constant oxide.

Titanium-coated cathode material has a higher capacitance per unit area than traditional aluminum electrolytic capacitor cathodes, in various embodiments. Some cathodes which are 98% aluminum purity or higher generally have capacitance per unit area of approximately 250 $uF/cm^2$ for 30 micron thick foil, with an oxide breakdown voltage in the 1-3 volt range. However, a cathode as described herein results in a capacitance per unit area which, in some embodiments, is as high as 1000 $uF/cm^2$ or more.

Advantageously, this provides a single cathode which services several layers of anodic foil without exceeding the oxide breakdown voltage. When using a traditional cathode to service several layers (2 or more) of anodic foil, the cathode voltage may rise as high as 5 or more volts, which is usually greater than the breakdown voltage. When this occurs, the aluminum cathode begins to form oxide by a hydration process which extracts oxygen from the water present in the electrolyte. The reaction produces hydrogen gas as a byproduct which in turn has the effect of creating an internal pressure within the capacitor causing an undesirable mechanical bulge in the layers from the capacitor stack, or in the case. Therefore, the titanium-coated cathode described above serves as a corrective mechanism for hydrogen generation.

Separator 202 is located between each anode stack 203A, 203B, . . . , 203N and cathode 201. In one embodiment, separator 202 consists of two sheets of 0.0005 inches thick kraft paper impregnated with an electrolyte. In some embodiments, separator 202 includes a single sheet or three or more sheets.

The electrolyte can be any suitable electrolyte for an electrolytic capacitor, such as an ethylene-glycol base combined with polyphosphates, ammonium pentaborate, and/or an adipic acid solute.

Illustrated is an anode stack 203A, 203B, . . . , 203N, but in various embodiments, anode stack 203A, 203B, . . . , 203N includes one, two, three or more anodes having a variety of anode shapes. Each anode has a major surface 151 and an edge face 150 generally perpendicular to major surface 151. Anodes 203A, 203B, . . . , 203N are generally foil structures and can include aluminum, tantalum, hafnium, niobium, titanium, zirconium, and combinations of these metals.

Figure 6:
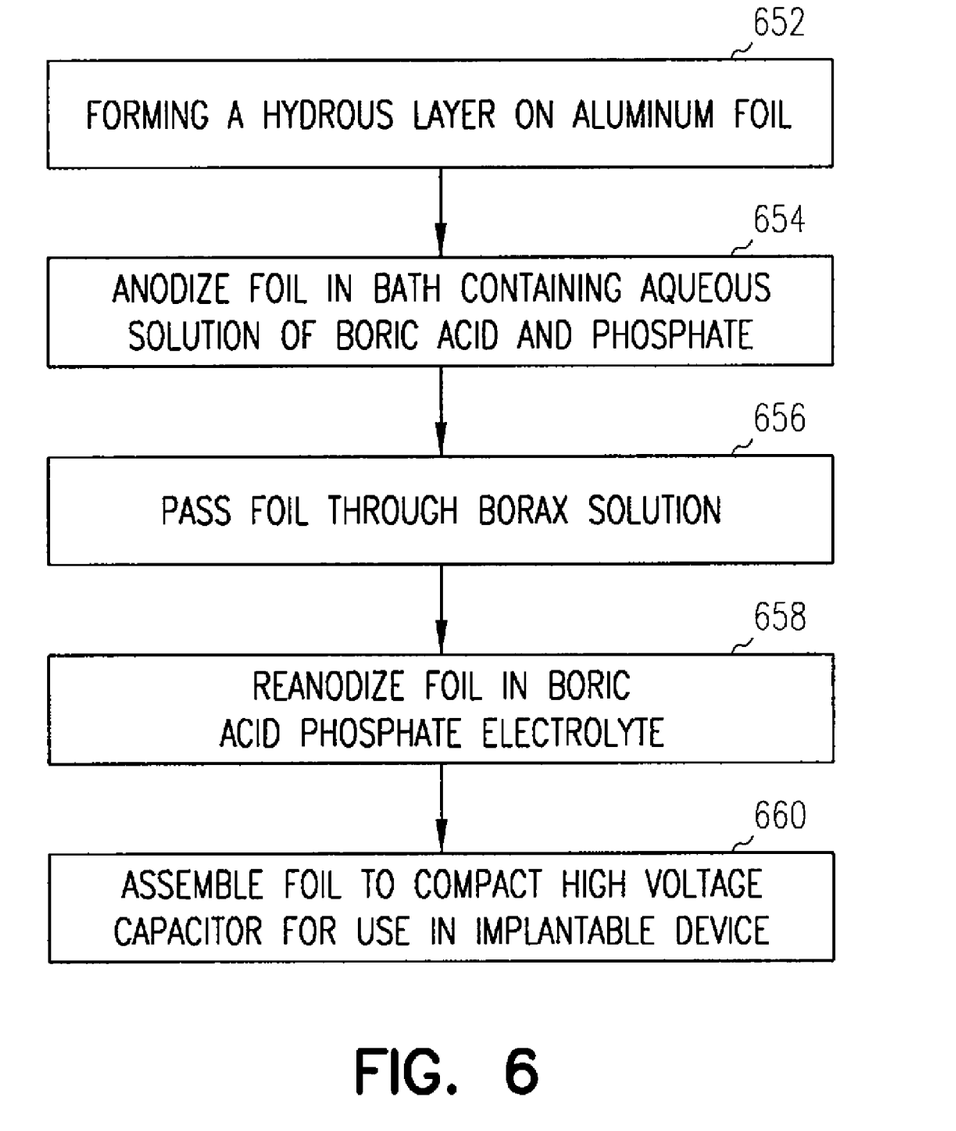
FIG. 6 illustrates an example process for the anodization of aluminum electrolytic capacitor foil, according to the present subject matter.

In one embodiment, anode foils 203A, 203B, . . . , 203C are high formation voltage anode foils, examples of which are discussed in this application, including the discussion associated with example FIG. 6. In various embodiments, the anode foils are medium and/or low formation voltage foils. In one embodiment, the major surface of each anode foil 203A, 203B, . . . , 203N is roughened or etched to increase its microscopic surface area. This increases the microscopic surface area of the foil with no increase in volume. Various embodiments use tunnel-etched, core-etched, and/or perforated-core-etched foil structures. Various embodiments utilize other foil compositions and classes of foil compositions.

Depending on which process is used to construct the anode, various surfaces are coated with a dielectric. For example, in embodiments where the anode shapes are punched from a larger sheet which has previously been coated with dielectric, only the surfaces which have not been sheared in the punching process are coated with dielectric. But if the dielectric is formed after punching, in various embodiments, all surfaces are coated. In some embodiments, anodes are punched from a larger sheet to minimize handling defects due to handling during the manufacturing process. For example, if a larger sheet is used as a starting material from which a number of anode layers are punched, machines or operators can grasp areas of the starting material which is not intended to form the final anode. Generally, in embodiments where the entire anode is not covered with dielectric, the anode is aged to restore the dielectric.

Various embodiments of the present subject matter include anode foils, or layers, which are only partially etched. For example, the example anodes illustrated include an substantially unetched portion 110A, 110B, . . . , 110N, and an etched portion 108A, 108B, . . . , 108N. In various embodiments, the etched portion 108A, 108B, . . . , 108N and the unetched portion are separated by an etch gradient 109A, 109B, . . . , 109N. In various embodiments, the etch gradient is structured to reduce bending stress at the etch gradient 109. Anode 203A, 203B, . . . , 203N includes an etch gradient structure as described on or around pages 32-34, 115-119 of Provisional U.S. Patent Application Ser. No. 60/588,905. The teachings of those pages are incorporated herein by reference, but not by way of limitation.

In various embodiments, the present subject matter includes anodes 203A, 203B, . . . , 203N, which have unetched portions 110A, 110B, . . . , 110N on a single side of an anode layer. In some embodiments, these single-sided portions are substantially constrained to a single approximately planar face 151 of an anode. Additionally, single sided portions in some embodiments are primarily constrained to a first approximately planar face 151 of an anode, with sections of the unetched portion extending to second approximately planar face of the anode. In various embodiments, a second approximately planar face includes edge 150.

Figure 3:
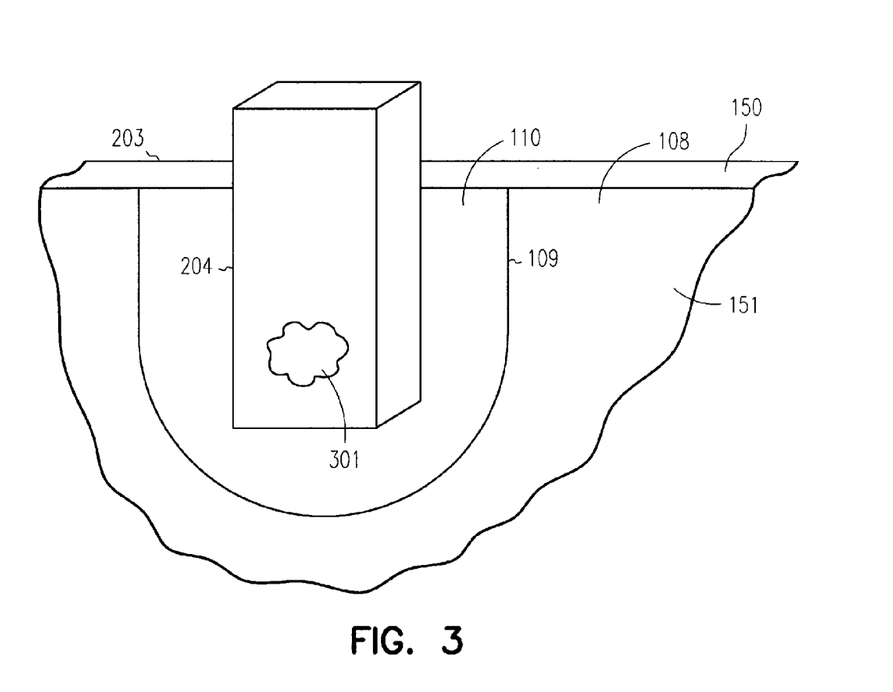
FIG. 3 is a perspective view of a connection member connected to a capacitor layer, according to one embodiment of the present subject matter.

FIG. 3 is a partial perspective view of a connection member connected to a capacitor layer, according to one embodiment of the present subject matter. In various embodiments, anode layer includes an etched portion 108, and an unetched portion 110. In various embodiment, the etched portion and the unetched portion are separated by an etch gradient 109. The etch gradient 109 can be sudden, assuming a line-shaped appearance. Additionally, etch gradient may define a gradual change, including a half-tone of varying percentages of etch. Although the unetched portion 110 is defined as semi-circular in the example illustration, other shapes are within the scope of the present subject matter. Additionally, in some embodiments, an unetched portion 110 is constrained to major surface 151, and in additional embodiments, extends to edge face 150. In some embodiments, etch gradient 109 is constrained to a major surface 151.

In various embodiments, a connection member 204 is connected to the unetched portion of the anode 203. In various embodiments, the connection between the connection member 204 and the anode 203 is solid-state. Solid state welds are known in the art. In some embodiments, the connection includes at least one joint 301 formed by a cold welding or staking process. In one embodiment, the joining process uses a small staking point. For example, in one embodiment, each joint 301 is a micro-stake joint approximately 0.015" (0.381 mm) in diameter. In other embodiments, joint 301 is less than or equal to approximately 0.030" (0.762 mm) in diameter. In some embodiments, joint 301 can range from approximately 0.005" (0.127 mm) to approximately 0.030" (0.762 mm). In some embodiments, joint 301 can range from approximately 0.010" (0.254 mm) to approximately 0.020" (0.508 mm). In various embodiments, joint 301 is a single weld, and in additional embodiments, joint 301 included multiple welds. For example, one type of multiple weld uses two stakes concurrently, on different areas of connection member 204. The following commonly assigned Provisional U.S. Patent Application, "Method and Apparatus for Single High Voltage Aluminum Capacitor Design," Ser. No. 60/588,905, filed on Jul. 16, 2004, includes additional examples of solid state connections at or around pages 16-23, 38, the examples incorporated herein by reference, but not by way of limitation.

Figure 4:
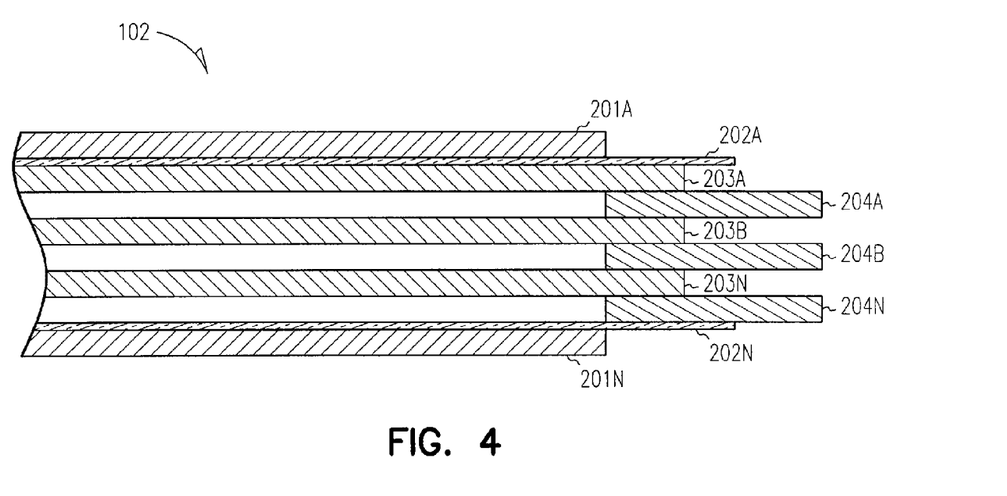
FIG. 4 is a partial side view of a capacitor stack, according to one embodiment of the present subject matter.

FIG. 4 is a side view of a partial capacitor stack, according to one embodiment of the present subject matter. In various embodiments, the view shows a cathode layers 201A, . . . , 201N, separator layers 202A, . . . , 202N, anode layers 203A, 203B, . . . , 203N, and connection members 204A, 204B, . . . , 204N. The illustration includes one configuration having 2 cathodes, 2 separator layers, three anodes, and three connection members, but other numbers of components comprising capacitor stack 102 are within the scope of the present subject matter.

Figure 5:
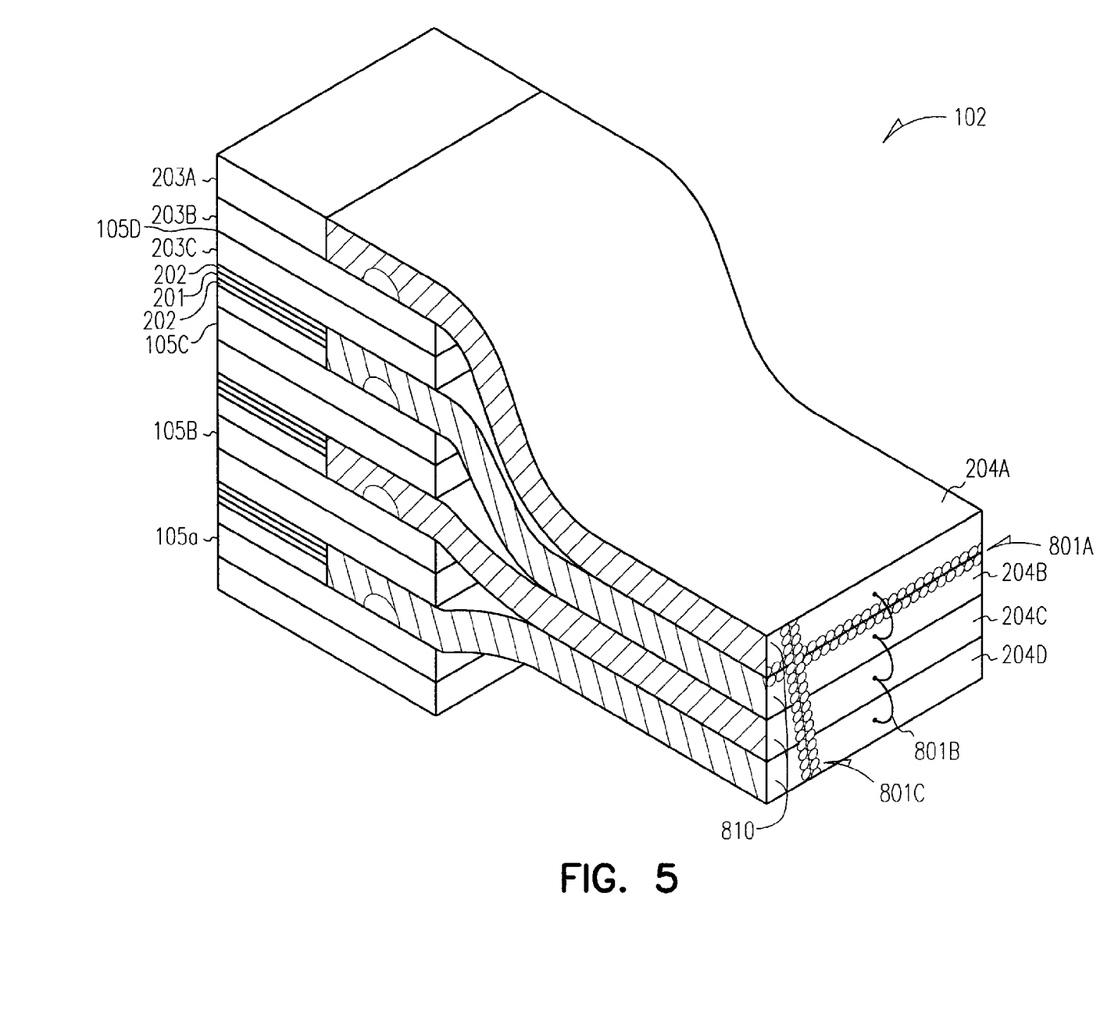
FIG. 5 is a partial cross-sectional isometric view of a capacitor having edge-connected connection members, according to one embodiment of the present subject matter.

FIG. 5 shows a connection member-to-connection member connection of a capacitor stack 102, according to one embodiment of the present subject matter. In the partial view shown, each capacitor element 105A-105D has a respective tab or connection member 204A-204D attached to it by an attachment method. In one embodiment, micro-staking is used to connect the connection members. In one embodiment, each connection member 204A-204D is approximately 0.004" (0.1016 mm) thick to fill the notch of anode foil 203A, which is 0.004" (0.1016 mm) thick. In other embodiments, the anode foil and the cathode and paper assembly have different thicknesses and so does the connection member.

Each connection member 204A-204D is positioned so that an exposed front edge face 810 of each connection member is proximal with an exposed front edge face of its neighboring connection members, forming a connection surface, such as an anode connection surface. In some embodiments, the edge faces 810 are cut to be flush with each other.

In various embodiments, each connection member 204A-204D is connected to its neighboring connection members along their respective front faces 810. This connection is a conductive interconnect. A conductive interconnect can include melted base material, as well as melted filler material, and can include a secondary structure, such as a metal bar, which is welded to each individual layer. Three embodiments of edge connections 801 are shown. Connections 801 include a laser seam edge-weld 801A, a wire bonded connection 801B, and a laser cross-wise edge-weld 801C. However, other joining processes are used. For example, in one embodiment, edge connection 801 is provided by an ultrasonic edge weld. Additionally, in various embodiments, an interconnection member, such as a ribbon of aluminum, is disposed along the front edge face 810 and connected to the front edge face 810.

In one embodiment, laser edge-weld 801A is provided by a Lumonics JK702 Nd-YAG laser welder using settings of approximately 1.4 Joules at a frequency of 100 hertz. The laser power is approximately 110 Watts, the pulse height is approximately 22%, and the pulse width is approximately 1.4 msec. In various embodiments, the pulse width ranges from about 1.0 ms to about 2.5 ms and the energy level ranges from about 0.8 J to about 2.0 J. In the present process, the connection members are held together in a vice, and the laser beam diameter is approximately 0.011" (0.279 mm). The laser beam is applied along the edge of connection members 204A-204D in a longitudinal manner incrementing to the left or to the right. Alternatively, other welding patterns are used to edge-weld connection members 204A-204D. In some embodiments, the connection members are welded along the horizontal axis, perpendicular to the edges of the connection members 204A-204D. (As shown in cross-wise edge-weld 801C).

In varying embodiments, edge-connecting connection members 204A, 204B, 204C, and 204D to each other provides a better electrical connection than crimping them together. Moreover, edge-connection 801, in various embodiments, creates a planar surface for attachment of a feedthrough terminal. One example of a feedthrough terminal includes a planar attachment surface. Additional examples include a ribbon connection member. The surface for connection improves manufacturing by reducing the difficulty of attaching a terminal to a plurality of anodes.

FIG. 6 illustrates an example process for the anodization of aluminum electrolytic capacitor foil, according to the present subject matter. In varying embodiments, the present subject matter is capable of producing anodized aluminum electrolytic capacitor foil at a formation voltage from about 200 volts to about 760 volts, which can result in a capacitor with a working voltage from about 150 volts to about 570 volts. For example, the present subject matter encompasses aluminum oxide formed at between approximately 600 volts and approximately 760 volts. Additionally, the present subject matter encompasses embodiments where anodization occurs from about 653 volts to about 720 volts. Additionally, the present subject matter encompasses embodiments wherein anodization occurs from about 667 volts to about 707 volts during formation.

Varied processes can be utilized to produce the aluminum foil of the present subject matter. For example, one process includes forming a hydrous oxide layer on an aluminum foil by immersing the foil in boiling deionized water 652. The aluminum foil is also subjected to electrochemical anodization in a bath containing an anodizing electrolyte 654 composed of an aqueous solution of boric acid, a phosphate, and a reagent. Additionally, the anodizing electrolyte contains a phosphate. In various embodiments, the anodizing electrolyte is at a pH of approximately 4.0 to approximately 6.0. In some examples, the foil is passed through a bath containing a borax solution 656. Borax, in various embodiments, includes a hydrated sodium borate, $Na_2B_4O_7 \cdot 10H_2O$, and is an ore of boron.

In varying embodiments, the foil is reanodized in the boric acid-phosphate electrolyte previously discussed 658. In various embodiments of the present subject matter, the process produces a stabilized foil suitable for oxide formation of up to approximately 760 volts.

In various embodiments, the anodizing electrolyte used in block 654 and 656 contains about 10 grams per liter to about 120 grams per liter of boric acid and approximately 2 to approximately 50 parts per million phosphate, preferably as phosphoric acid, and sufficient alkaline reagent to lower the resistivity to within approximately 1500 ohm-cm to approximately 3600 ohm-cm and increase the pH from about 4.0 to about 6.0 for best anodization efficiency and foil quality.

In some embodiments, the borax bath contains 0.001 to 0.05 moles/liter of borax. Because the anodizing electrolyte is acidic, in various embodiments, the borax bath is buffered with sodium carbonate to prevent lowering of the pH by dragout of the acidic electrolyte. Additionally, in various embodiments, the borax bath is buffered to lower its resistivity. In one example, the pH of the bath is from about 8.5 to about 9.5, and the temperature is at least approximately 80 degrees Celsius. In varying embodiments, the sodium concentration is approximately 0.005 to approximately 0.05M, preferably about 0.02 M. It should be noted that concentrations of less than approximately 0.005M are too dilute to control properly, and concentrations above approximately 0.05M increase the pH, resulting in a more reactive solution which degrades barrier layer oxide quality.

In varying embodiments of the present subject matter, the presence of at least approximately 2 parts per million phosphate in the acidic anodizing electrolyte is critical. For example, this presence initiates stabilization of the foil so that solely hydrous oxide dissolves in the alkaline borax bath, without damage to the barrier layer dielectric oxide. In varying embodiments, this lowers ESR (equivalent series resistance) of the anodized foil.

Additionally, in various embodiments, when the foil is reanodized following the alkaline borax bath, the foil surface is alkaline and reacts electrochemically with the phosphate, which, in various embodiments, results in the incorporation of phosphate into the dielectric oxide. In varying examples, the alkaline foil surface includes an alkaline metal aluminate, and in one embodiment includes a sodium aluminate. It should be noted that the amount of allowable phosphate in the anodizing electrolyte, in various embodiments, is inversely proportional to the voltage at which the foil is being anodized. For example, in one embodiment, using greater than approximately 24 parts per million results in failure during oxide formation at around 650 volts. In embodiments where approximately 50 parts per million of phosphate is exceeded, the electrolyte scintillates at the foil interface, resulting in damaged, unstable foil. One benefit of the present subject matter is that an electrode is produced which can tolerate a high formation voltage without scintillation at the boundary layer of the foil. It should be noted that anodization temperature should be maintained from about 85 degrees Celsius to about 95 degrees Celsius, as variance outside of these values results in a the barrier layer oxide of lower quality, and foil corrosion.

Various aspects of the present subject matter include performance properties which enable the capacitor to function as a single capacitor in an implantable cardioverter defibrillator 660. For example, by constructing the capacitor stack with the methods and apparatus contained in these teachings, one may construct a capacitor which is suited for use as the sole capacitor used for powering therapeutic pulses in an implantable cardioverter defibrillator. By using a single capacitor, instead of two capacitors which are connected in series, the present subject matter contributes to weight and size reductions.

Figure 7:
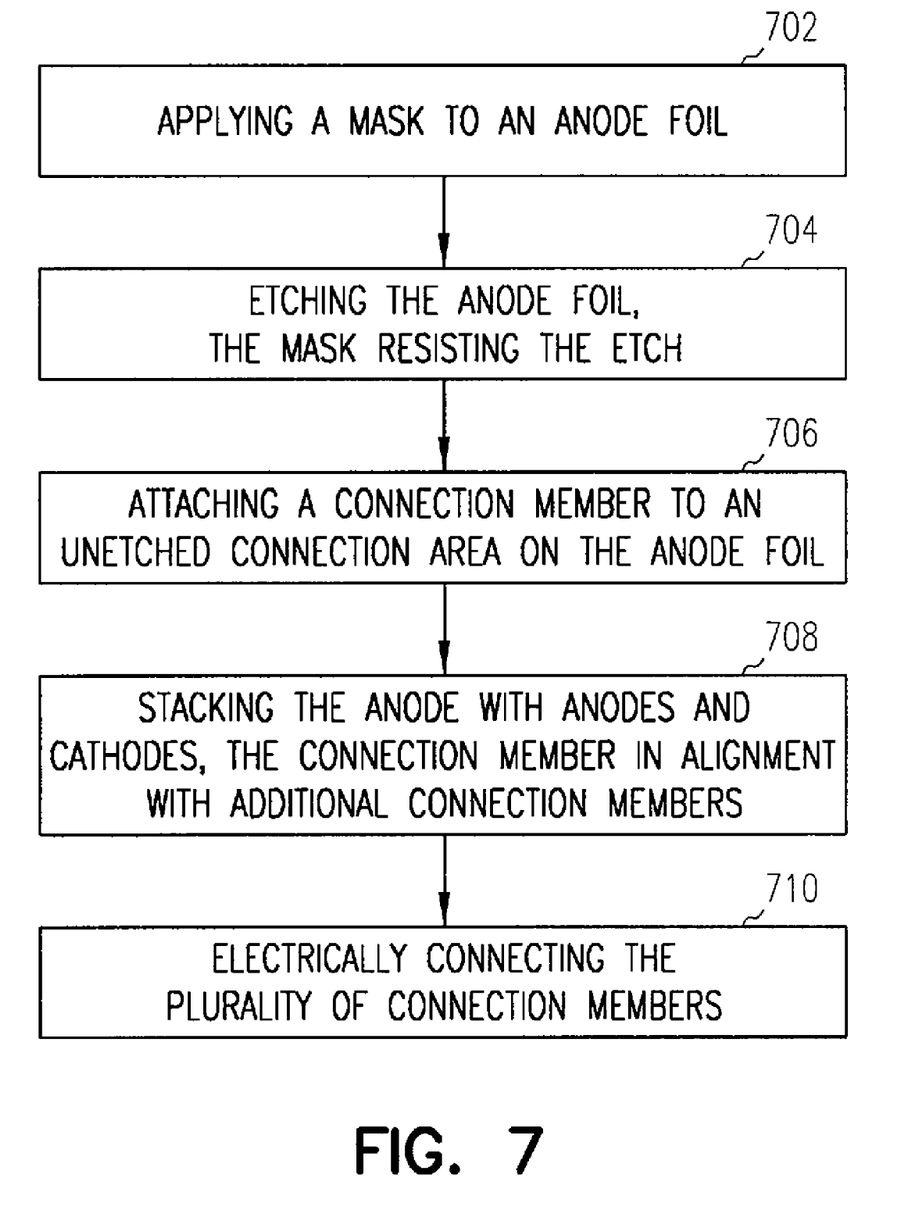
FIG. 7 illustrates a block diagram of one process for forming an anode with a connection member, according to one embodiment of the present subject matter.

FIG. 7 illustrates a block diagram of one method of making at least one partially etched anode, according to various embodiments of the present subject matter. The present subject matter includes applying a mask to an anode foil, 702. In various embodiments, applying a mask to an anode foil includes application of a mask as is discussed on or around pages 32-34 of related Provisional U.S. Patent Application "Method and Apparatus for High Voltage Aluminum Capacitor Design," Ser. No. 60/588,905, filed on Jul. 16, 2004, incorporated herein by reference, but not by way of limitation.

Various additional embodiments include etching the anode 704. Etching the anode increases the surface roughness. In one example, the present subject matter includes an unetched connection area formed by the process of applying a mask to an anode foil, etching the anode foil, and removing the mask. In one embodiment, the mask is formed by curing a resin on an anode.

In various embodiments, the present subject matter includes attaching a connection member to an unetched connection area on the anode foil 706. The present subject matter additionally includes stacking the anode with anodes and cathodes, the connection member in alignment with additional connection members 708.

In a first example, the present subject matter includes attaching a first connection member to an unetched connection area on a single side of a first anode layer. The example includes forming a capacitor stack by aligning the first anode layer with at least a second anode layer, the second anode layer having at least a second connection member, the first connection member and the second connection member for electrical connection of the anode layer to the plurality of capacitor electrodes, and aligning the first connection member and the second connection member to define an anode connection surface.

In a second example, the present subject matter includes forming a capacitor stack by assembling the first anode layer with at least one cathode layer, the assembled first anode layer and at least one cathode layer defining an element, and stacking at least two elements in alignment.

In a third example, the present subject matter includes forming a capacitor stack by positioning the first connection member and the second connection member so that the first connection member and the second connection member are separated by a distance, the distance approximately equal to the thickness of the second anode layer. Additionally, the third examples includes aligning the first connection member and the second member by bending them together, putting the first connection member and the second connection member into adjacent positions.

In these examples, as well as in additional embodiments not enumerated here, a connection member is more malleable than is an etched surface such as an etched anode surface. By including a connection member which has improved malleability, various processes can deform the connection members into forming an aligned connection surface without damaging structure. Damaged structure, in embodiments without malleable structures, includes cracked sections of anodes which do not deform as elastically under bending stress as is needed for a process.

In additional embodiments, the present subject matter includes electrically connecting the plurality of connection members 710. This can include connections using welds with or without filler metal. This can also include connections using an additional structure, such as a bar welded to the connection members. In various embodiments, one example includes connecting an anode interconnect to the anode connection surface. An anode connection surface, in various embodiments, is formed by aligning two or more edges, such as connection member edges, adjacently, so that the edges are positioned proximal. The example FIG. 5 demonstrates a surface 810 which can serve as one example of an anode connection surface.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and various embodiments, will be apparent to those of skill in the art upon reviewing the above description. The scope of the present subject matter should be determined with reference to the appended claims, along with the full scope of equivalents to which such claims are entitled.

What is claimed is:

1. An apparatus, comprising:
 a capacitor stack including:
  a first partially etched anode including a first substantially unetched portion;
  a first connection member stacked onto the first partially etched anode and joined to the first substantially unetched portion;
  a second anode stacked onto the first connection member and onto a cathode that is stacked onto the first anode beside the first connection member;
  a first separator layer disposed between the first anode and the cathode; and
  a second separator layer disposed between the cathode and the second anode,
  wherein the thickness of the first separator layer, the second separator layer and the cathode is less than or approximately equal to the thickness of the first connection member.

2. The apparatus of claim 1, wherein the first connection member is connected to the first substantially unetched portion of the first partially etched anode via a stake weld.

3. The apparatus of claim 1, further comprising:
 a first element including the first partially etched anode and the cathode; and
 a second element including the second anode and at least a second planar cathode,
 wherein the first element and the second element are stacked in alignment, with a first element edge face and a second element edge face defining a connection surface adapted to join the first element to the second element.

4. The apparatus of claim 1, further comprising:
 a case, the capacitor stack disposed in the case;
 an anode terminal connected to at least one anode of the stack and sealed to the case; and
 a cathode terminal connected to at least one cathode of the capacitor stack and sealed to the case,
 wherein the case is hermetically sealed.

5. The apparatus of claim 4, wherein the capacitor stack, the anode terminal, and the cathode terminal are adapted to provide from about 5.3 joules per cubic centimeter of capacitor stack volume to about 6.3 joules per cubic centimeter of capacitor stack volume.

6. The apparatus of claim 5, wherein the capacitor stack, the anode terminal, and the cathode terminal are adapted to provide approximately 5.8 joules per cubic centimeter of capacitor stack volume.

7. The apparatus of claim 1, wherein the first connection member and a second connection member, coupled to the second anode, are in alignment.

8. The apparatus of claim 7, wherein the first connection member and the second connection member define a connection surface for connection of the first partially etched anode and the second anode.

9. The apparatus of claim 8, further comprising a weld disposed along the connection surface and joining the first and the second anode.

10. The apparatus of claim 9, wherein the weld includes a laser weld.

11. An apparatus, comprising:
 a capacitor stack, comprising:
  a first substantially planar capacitor anode;
  a first connection member stacked onto the first substantially planar capacitor anode and connected to a substantially unetched portion of the first substantially planar capacitor anode;
  a second substantially planar capacitor anode stacked onto the first connection member and onto a cathode that is stacked onto the first substantially planar capacitor anode and beside the first connection member, the second anode in alignment with the first substantially planar capacitor anode;
  a first separator layer disposed between the first anode and the cathode; and
  a second separator layer disposed between the cathode and the second anode,
 wherein the thickness of the first separator layer, the second separator layer and the cathode is less than or approximately equal to the thickness of the first connection member.

12. The apparatus of claim 11, further comprising an interconnection member that interconnects the first connection member and a second connection member that is coupled to the second substantially planar capacitor anode.

13. The apparatus of claim 11, further comprising gradient means for transition between an etched portion of the first substantially planar capacitor electrode and the substantially unetched portion of the first substantially planar capacitor electrode.

14. The apparatus of claim 11, further comprising a weld connecting the first connection member and the second connection member.

15. The apparatus of claim 14, wherein the weld is formed by the process of laser welding.

16. The apparatus of claim 14, wherein the weld includes a solid-state weld.

17. A first substantially planar anode electrode and a second substantially planar anode electrode, the first substantially planar anode electrode including a first substantially unetched portion that is connected to a first connection member that is sandwiched between the first substantially planar anode electrode and the second substantially planar anode electrode, with a cathode that is also sandwiched between the first substantially planar anode electrode and the second substantially planar anode electrode, the cathode beside the first connection member and electrically insulated from the first substantially planar anode electrode, the second substantially planar anode electrode and the connection member, the first substantially unetched portion produced by a process comprising:

depositing a curable resin mask onto a substantially planar anode electrode;

curing the curable resin mask to the substantially planar anode electrode;

etching the substantially planar anode electrode, the cured mask restricting the etch;

removing the cured mask from the substantially planar anode electrode; and anodizing the substantially planar anode electrode.

18. The substantially planar anode electrode of claim 17, further disposed in a first element including the first anode electrode and the cathode, with a second element comprising the second anode electrode and at least a second planar cathode, wherein the first element and the second element are stacked in alignment, with a first element edge face and a second element edge face defining a connection surface adapted to join the first element and the second element.

19. The substantially planar anode electrode of claim 18, disposed in a case, with an anode terminal connected to the first substantially planar anode electrode; and with a cathode terminal connected to the cathode, wherein the case is hermetically sealed.

20. The substantially planar anode electrode of claim 19, adapted to provide a packaged energy density of from about 5.3 joules per cubic centimeter of capacitor stack volume to about 6.3 joules per cubic centimeter of capacitor stack volume.

21. The substantially planar anode electrode of claim 20, adapted to provide a package energy density of approximately 5.8 joules per cubic centimeter of capacitor stack volume.

\* \* \* \* \*

UNITED STATES PATENT AND TRADEMARK OFFICE
CERTIFICATE OF CORRECTION

PATENT NO. : 7,532,456 B2 Page 1 of 1
APPLICATION NO. : 11/379284
DATED : May 12, 2009
INVENTOR(S) : Poplett It is certified that error appears in the above-identified patent and that said Letters Patent is hereby corrected as shown below:

In column 1, line 8, after "continuation" insert -- of --.

Signed and Sealed this

Twenty-eighth Day of July, 2009

JOHN DOLL
*Acting Director of the United States Patent and Trademark Office*